United States Patent
Majdali et al.

(10) Patent No.: US 10,898,601 B2
(45) Date of Patent: Jan. 26, 2021

(54) SYSTEMS AND METHODS FOR SANITIZING AMUSEMENT PARK EQUIPMENT

(71) Applicant: Universal City Studios LLC, Universal City, CA (US)

(72) Inventors: David Majdali, Orlando, FL (US); John Ugrin, Orlando, FL (US)

(73) Assignee: Universal City Studios LLC, Universal City, CA (US)

( * ) Notice: Subject to any disclaimer, the term of this patent is extended or adjusted under 35 U.S.C. 154(b) by 231 days.

(21) Appl. No.: 15/937,631

(22) Filed: Mar. 27, 2018

(65) Prior Publication Data

US 2019/0298866 A1    Oct. 3, 2019

(51) Int. Cl.
*A61L 2/10* (2006.01)
*A61L 2/18* (2006.01)
(Continued)

(52) U.S. Cl.
CPC .... *A61L 2/10* (2013.01); *A61L 2/18* (2013.01); *A61L 2/22* (2013.01); *A61L 2/24* (2013.01); (Continued)

(58) Field of Classification Search
CPC ..... A61L 2/10; A61L 2/22; A61L 2/18; A61L 2/24; A61L 2202/122; A61L 2202/16;
(Continued)

(56) References Cited

U.S. PATENT DOCUMENTS 5,016,662 A * 5/1991 Crotts ............... B60S 3/04
                                                134/123
5,076,304 A * 12/1991 Mathews ........... B60S 3/04
                                                134/123
(Continued)

FOREIGN PATENT DOCUMENTS

CH          293571 A      9/1953
DE         4205113 C1     4/1993
(Continued)

OTHER PUBLICATIONS

The Hepacart Blog, Information on Specialized Infection Control, Dust Containment Products, and Facility Management, What is Far-UV Sterilray™?, Jun. 20, 2017, pp. 1-7, http://www.hepacart.com/blog/what-is-far-uv-sterilray.
(Continued)

*Primary Examiner* — Regina M Yoo
(74) *Attorney, Agent, or Firm* — Fletcher Yoder, P.C.

(57) ABSTRACT

A sanitization system for an amusement park includes a sanitization station disposed along a ride path of a ride of the amusement park. The sanitization station includes a housing configured to receive a ride vehicle as the ride vehicle travels along the ride path, an ultraviolet light source configured to transmit ultraviolet light toward a surface of the ride vehicle, and a control system configured to detect a position of the ride vehicle along the ride path and to activate the ultraviolet light source when the control system determines that the ride vehicle is positioned at a first particular position relative to the housing.

20 Claims, 10 Drawing Sheets

(51) Int. Cl.
*A61L 2/24* (2006.01)
*A63G 31/00* (2006.01)
*A61L 2/22* (2006.01)
*A63G 7/00* (2006.01)

(52) U.S. Cl.
CPC ............... *A63G 7/00* (2013.01); *A63G 31/00* (2013.01); *A61L 2202/11* (2013.01); *A61L 2202/121* (2013.01); *A61L 2202/122* (2013.01); *A61L 2202/14* (2013.01); *A61L 2202/15* (2013.01); *A61L 2202/16* (2013.01); *A61L 2202/17* (2013.01)

(58) Field of Classification Search
CPC ........... A61L 2202/11; A61L 2202/121; A61L 202/14; A61L 2202/15; A61L 2202/17; A63G 7/00; A63G 31/00
See application file for complete search history.

(56) References Cited

U.S. PATENT DOCUMENTS

| | | | |
|---|---|---|---|
| 6,039,928 A | 3/2000 | Roberts | |
| 6,095,438 A * | 8/2000 | Fratello | B60S 3/04 118/314 |
| 6,283,135 B1 * | 9/2001 | Fratello | B60S 3/04 134/123 |
| 7,160,566 B2 | 1/2007 | Fink et al. | |
| 7,791,044 B1 | 9/2010 | Taylor et al. | |
| 9,144,618 B2 | 9/2015 | Kreitenberg | |
| 9,433,695 B2 * | 9/2016 | Aamodt | A61L 9/14 |
| 9,764,245 B2 * | 9/2017 | Weston | A63G 31/007 |
| 10,160,622 B2 * | 12/2018 | Kim | A61L 2/18 |
| 2002/0085947 A1 | 7/2002 | Deal | |
| 2003/0150475 A1 | 8/2003 | Abrams et al. | |
| 2005/0022844 A1 | 2/2005 | Field et al. | |
| 2006/0011220 A1 * | 1/2006 | Mueller | A47F 10/04 134/45 |
| 2007/0012340 A1 * | 1/2007 | Jones | A61L 2/10 134/45 |
| 2007/0057197 A1 | 3/2007 | Chor | |
| 2007/0164232 A1 | 7/2007 | Rolleri et al. | |
| 2007/0258851 A1 | 11/2007 | Fogg et al. | |
| 2007/0272150 A1 * | 11/2007 | Swoboda | F26B 3/28 118/642 |
| 2007/0289616 A1 * | 12/2007 | McCadden | B05B 3/0463 134/123 |
| 2008/0118395 A1 | 5/2008 | Benedek | |
| 2008/0178412 A1 * | 7/2008 | Kiter | A61L 2/10 15/309.2 |
| 2008/0199354 A1 | 8/2008 | Gordon | |
| 2008/0289649 A1 | 11/2008 | Woytkiw | |
| 2009/0304553 A1 | 12/2009 | Gordon | |
| 2009/0311149 A1 | 12/2009 | Freedgood | |
| 2010/0266446 A1 | 10/2010 | Constantacos | |
| 2011/0158862 A1 * | 6/2011 | Kim | B66B 31/02 422/292 |
| 2011/0168898 A1 | 7/2011 | Statham et al. | |
| 2011/0243789 A1 | 10/2011 | Roberts | |
| 2011/0293484 A1 | 12/2011 | Stausgaard et al. | |
| 2012/0273340 A1 | 11/2012 | Felix | |
| 2013/0129567 A1 | 5/2013 | Gray | |
| 2014/0030161 A1 | 1/2014 | Alovisi | |
| 2014/0096801 A1 | 4/2014 | McCormick et al. | |
| 2014/0158910 A1 | 6/2014 | Fletcher | |
| 2015/0190537 A1 | 7/2015 | Kerr | |
| 2015/0209459 A1 | 7/2015 | Kreitenberg | |
| 2015/0217010 A1 | 8/2015 | Whitney | |
| 2015/0290346 A1 | 10/2015 | Kassel et al. | |
| 2016/0136529 A1 * | 5/2016 | Weston | A63G 31/007 472/117 |
| 2016/0220716 A1 | 8/2016 | Childress et al. | |
| 2016/0346704 A1 | 12/2016 | Wagner | |
| 2017/0000915 A1 | 1/2017 | Cottone | |
| 2017/0043044 A1 | 2/2017 | Sobhy | |
| 2018/0099842 A1 * | 4/2018 | Kim | A61L 2/26 |

FOREIGN PATENT DOCUMENTS

| | | |
|---|---|---|
| DE | 102009040765 A1 | 2/2011 |
| EP | 0772226 A2 | 5/1997 |
| FR | 2129901 A1 | 11/1972 |
| KR | 101408941 B1 | 6/2014 |
| KR | 20150017544 A | 2/2015 |
| WO | 0035723 | 6/2000 |
| WO | 2010060079 A1 | 5/2010 |

OTHER PUBLICATIONS

Columbia University Medical Center Newsroom, Narrow Wavelength of UV Light Safely Kills Drug-Resistant Bacteria, Jun. 8, 2016, pp. 1-5, http://newsroom.cumc.columbia.edu/blog/2016/06/08/narrow-wavelength-uv-light-safely-kills-drug-resistant-bacteria-2/.

Cohen, Jon, Could ultraviolet lamps slow the spread of flu?, Science Magazine, Jan. 3, 2018, pp. 1-4, http://www.sciencemag.org/news/2018/01/could-ultraviolet-lamps-slow-spread-flu?utm_source=newsfromscience&utm_medium=facebook-text&utm_campaign=flulamp-17172.

PCT/US2018/061332 Search Report and Written Opinion dated Feb. 5, 2019.

* cited by examiner

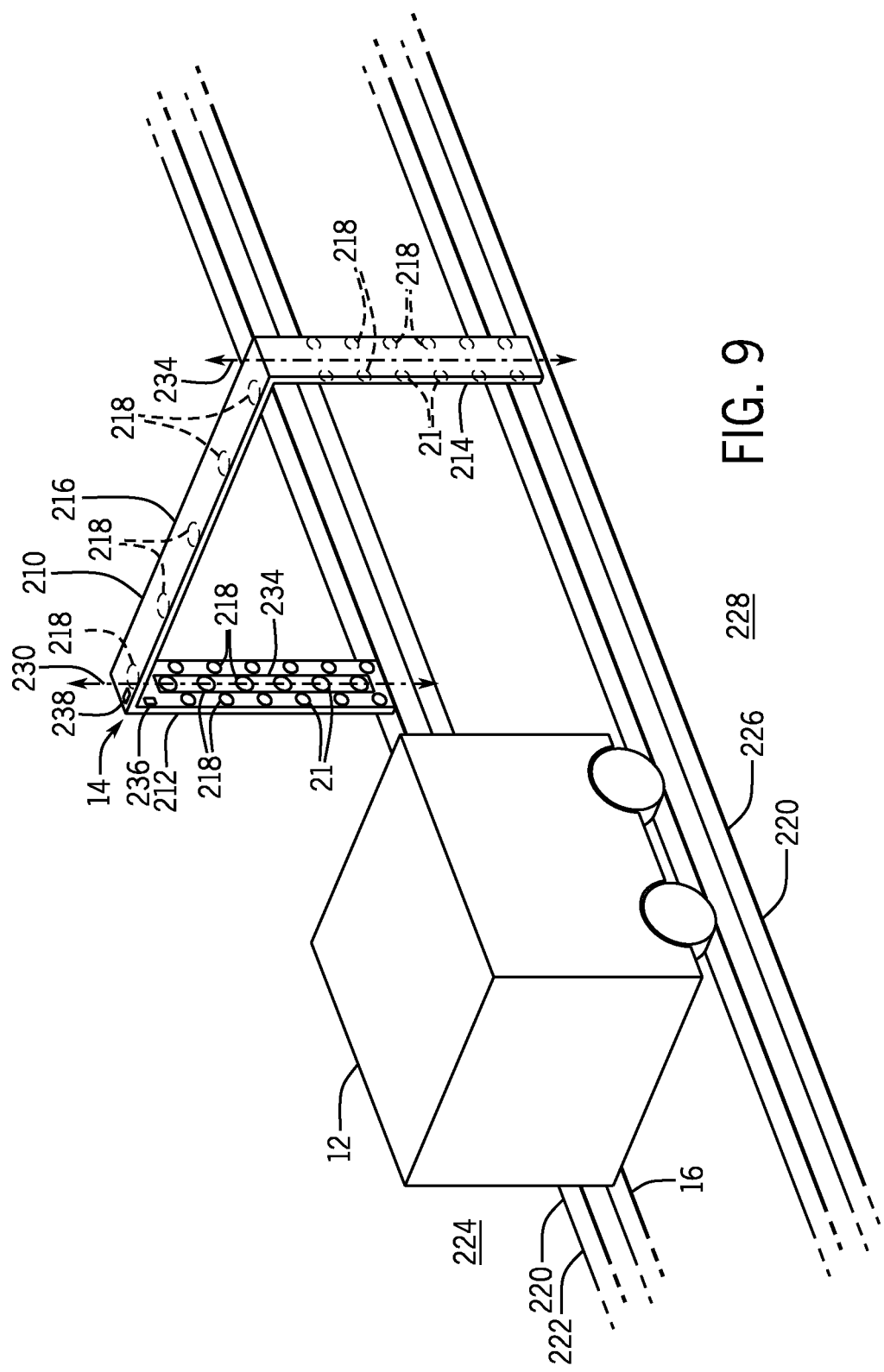

SYSTEMS AND METHODS FOR SANITIZING AMUSEMENT PARK EQUIPMENT

BACKGROUND

The present disclosure relates generally to the field of amusement parks. More specifically, embodiments of the present disclosure relate to a sanitization system for an amusement park.

This section is intended to introduce the reader to various aspects of art that may be related to various aspects of the present disclosure, which are described below. This discussion is believed to be helpful in providing the reader with background information to facilitate a better understanding of the various aspects of the present disclosure. Accordingly, it should be understood that these statements are to be read in this light, and not as admissions of prior art.

Amusement parks contain a variety of rides and other features that provide unique experiences to each park guest. In some cases, ride cars, handles, interactive components, or other features that guests contact may accumulate bacteria or other undesirable substances. Accordingly, amusement parks may include processes for removing such substances from surfaces that guests frequently contact. It is now recognized that existing cleaning processes are time consuming, and thus, may increase wait times for guests to experience the ride or attraction. Additionally, it is also recognized that some existing cleaning processes may be performed only during off hours of the amusement park.

SUMMARY

Certain embodiments commensurate in scope with the originally claimed subject matter are summarized below. These embodiments are not intended to limit the scope of the disclosure, but rather these embodiments are intended only to provide a brief summary of certain disclosed embodiments. Indeed, the present disclosure may encompass a variety of forms that may be similar to or different from the embodiments set forth below.

In one embodiment, a sanitization system for an amusement park includes a sanitization station disposed along a ride path of a ride of the amusement park. The sanitization station includes a housing configured to receive a ride vehicle as the ride vehicle travels along the ride path, an ultraviolet light source configured to transmit ultraviolet light toward a surface of the ride vehicle, and a control system configured to detect a position of the ride vehicle along the ride path and to activate the ultraviolet light source when the control system determines that the ride vehicle is positioned at a first particular position relative to the housing.

In another embodiment, a system includes an amusement park ride having a ride path and a ride vehicle, wherein the ride vehicle is configured to transport a guest along the ride path in a direction of the ride, and wherein the ride path includes an unloading region for the guest to exit the ride vehicle and a loading region for the guest to enter the ride vehicle, and a sanitization station disposed along the ride path such that the sanitization station is past the unloading region and before the loading region of the ride path along the direction of the ride. The sanitization station includes a housing configured to receive the ride vehicle as the ride vehicle travels along the ride path, an ultraviolet light source configured to transmit ultraviolet light toward a surface of the ride vehicle, and a control system configured to detect a position of the ride vehicle along the ride path and to activate the ultraviolet light source when the control system determines that the ride vehicle is positioned at a particular position relative to the housing.

In another embodiment, a method includes detecting a position of a ride vehicle along a ride path of an amusement park ride using a sensor coupled to a control system, wherein the ride path includes an unloading region for a guest to exit the ride vehicle and a loading region for the guest to enter the ride vehicle, and activating, using the control system, an ultraviolet light source of a sanitization system to transmit ultraviolet light toward a surface of the ride vehicle upon detecting that the ride vehicle is traveling from the unloading region to the loading region of the ride path.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein:

FIG. 9 illustrates a perspective view of an embodiment of a movable ultraviolet light source assembly, in accordance with an aspect of the present disclosure;

DETAILED DESCRIPTION

Figure 1:
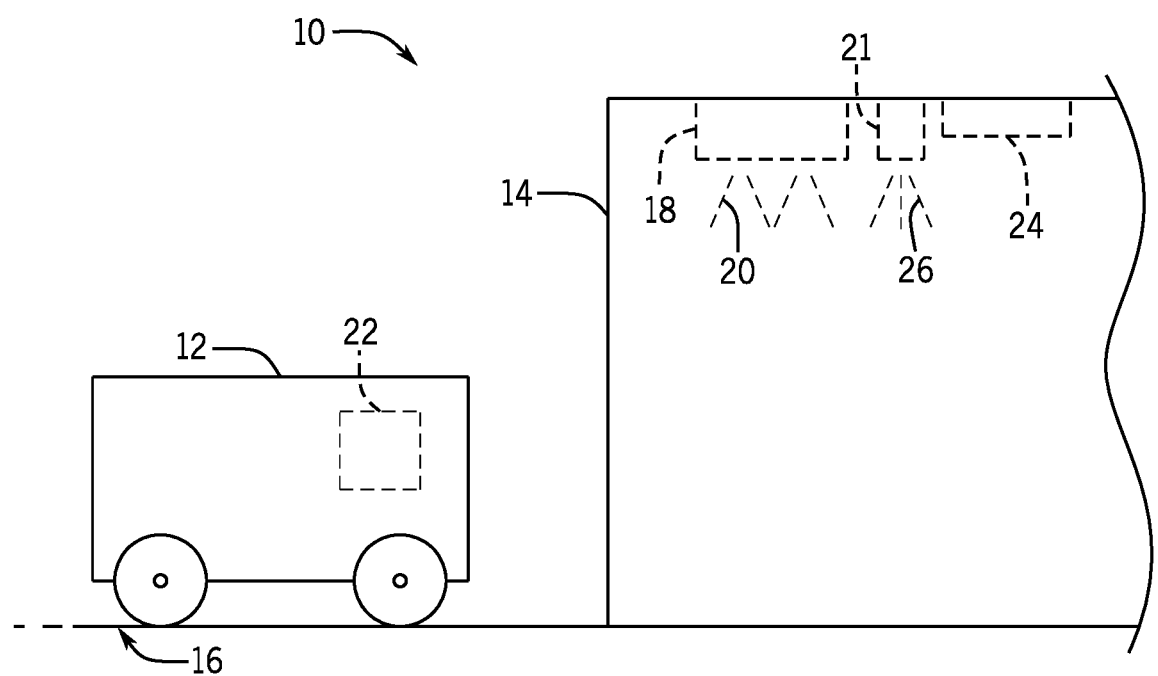
FIG. 1 illustrates an embodiment of a sanitization system for an amusement park ride, in accordance with an aspect of the present disclosure.

One or more specific embodiments of the present disclosure will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Amusement parks feature a wide variety of entertainment, such as amusement park rides, performance shows, and games. The different types of entertainment may include features that enhance a guest's experience at the amusement park. In some instances, amusement park rides, games, interactive equipment, and/or other features include surfaces (e.g., handles, knobs, seats, buttons, lap bars, seat belts) that guests frequently contact or touch. Such surfaces may accumulate bacteria and/or other undesirable substances as guests contact the surface and/or as the surfaces come into contact with air, water, mist, and/or spilled solids or liquids in an environment of the ride or feature. As such, amusement parks may have protocol in place for periodic sanitization of the surfaces to remove the bacteria or other undesirable substances. For example, amusement parks may utilize sanitization spray (e.g., soap or anti-bacterial liquid) to wipe down the surfaces which may be exposed to bacteria and other undesirable substances during off-hours of the amusement park (e.g., when the amusement park is closed). Further, amusement parks may otherwise shut down a specific attraction for cleaning the surfaces, thereby increasing wait times for guests of the amusement park.

Embodiments of the present disclosure are directed to an enhanced sanitization system for a ride of an amusement park that utilizes ultraviolet light to periodically remove bacteria and other undesirable substances from surfaces frequently contacted by guests. For example, the sanitization system may be disposed along a ride path between an unloading point for guests of the ride to exit a ride vehicle and a loading point for new guests to enter the ride vehicle. The sanitization system may be positioned along the ride path where guests are not in the ride vehicle (or waiting for access) based on normal operation. Thus, the sanitization system may be positioned such that guests do not block the ultraviolet light from reaching targeted surfaces. Additionally, the guests entering and exiting the ride vehicle may not be exposed to the ultraviolet light that ultimately sanitizes one or more surfaces of the ride vehicle. In some embodiments, ultraviolet light sources are disposed on actuated arms or movable members to position the ultraviolet light sources proximate to the surface to be cleaned. In other embodiments, the ultraviolet light sources are positioned within the ride vehicle and subsequently activated when the ride vehicle is positioned between the loading and unloading areas (e.g., traveling from a position past the unloading area to the loading area), such that guests do not block the ultraviolet light from reaching the targeted surfaces. While embodiments discussed below are generally directed to emitting ultraviolet light, it should be understood that the features that are described and illustrated as emitting the ultraviolet light may also be configured to emit sanitizing mists or sprays, such as a soap and water mixture or another cleaning solution, in addition to, or in lieu of, the ultraviolet light.

In any case, the sanitization system is configured to kill bacteria and at least partially remove other undesirable substances from surfaces of the ride vehicle that guests often contact. As such, the frequency and efficiency of sanitization of the amusement park ride increases, which may enhance the experience of guests visiting the amusement park.

Turning to the figures, FIG. 1 illustrates an embodiment of a sanitization system 10 for cleaning amusement park equipment, such as a ride vehicle 12. As shown in the illustrated embodiment of FIG. 1, the sanitization system 10 may include a sanitization station 14 positioned along a ride path 16 upon which the ride vehicle 12 travels. As discussed above, the sanitization station 14 may include an ultraviolet light source 18 configured to emit ultraviolet light 20 toward the ride vehicle 12 to kill bacteria and other undesirable substances from surfaces (e.g., seats, hand rails, interactive components, handles, knobs, buttons) of the ride vehicle 12 that the guests frequently contact. The ultraviolet light 20 contacts the surfaces of the ride vehicle 12 and removes the bacteria and other undesirable substances (e.g., viruses) that may be present on the surfaces. In some embodiments, the sanitization station 14 is disposed between a guest unloading region and a guest loading region of the ride path 16, such that guests of the amusement park ride do not cover (e.g., block) any portion of the surfaces of the ride vehicle 12. In other embodiments, the sanitization station 14 may be disposed along a portion of the ride path 16 where guests are situated in the ride vehicle 12 (e.g., between the loading region and the unloading region with respect to a direction of travel of the ride vehicle 12). As noted above, in some embodiments, the ultraviolet light source 18 may also be a source of a sanitizing mist or spray. For instance, the sanitization station 14 may include one or more nozzles 21 configured to direct a cleaning solution, such as a mixture of soap and water or water, toward the ride vehicle 12.

In certain embodiments, the ride vehicle 12 is configured to move along the ride path 16 and enter the sanitization station 14 to undergo a cleaning process periodically throughout operation of an amusement park ride that utilizes the ride vehicle 12. Accordingly, sanitization of the ride vehicle 12 is systematically performed during operating hours of the amusement park ride (e.g., when guests are riding the amusement park ride on other ride vehicles). In some cases, a speed of the ride vehicle 12 is slowed or reduced to substantially zero, such that the ride vehicle 12 is exposed to the ultraviolet light source 18 for a sufficient time to perform cleaning of the ride vehicle 12. For example, movement of the ride vehicle 12 may be stopped and/or otherwise reduced to ensure that the ride vehicle 12 is exposed to the ultraviolet light source 18 for a duration, such as between 1 second and 1 minute, between 5 seconds and 45 seconds, or between 10 seconds and 20 seconds, for example. In other embodiments, the ultraviolet light source 18 may move with the ride vehicle 12. For example, the ultraviolet light source 18 may be attached to a movable feature (e.g., a mechanical arm, a conveyor belt) that moves along with the ride vehicle 12 for a desired distance or time.

In any case, the ultraviolet light source 18 emits the ultraviolet light 20, which disinfects the surfaces of the ride vehicle 12. In some embodiments, the ultraviolet light 20 may include a predetermined wavelength suitable for killing common bacteria and/or other undesirable substances present on the surfaces of the ride vehicle 12. The wavelength of the ultraviolet light may be between 122 and 200 nanometers, thereby emitting far ultraviolet ("FUV") light to clean the surfaces of the ride vehicle 12. In other embodiments, the ultraviolet light 20 may include any suitable wavelength (e.g., between 10 and 400 nanometers).

Additionally or alternatively, the ride vehicle 12 may include an on-board sanitization component 22 that also emits the ultraviolet light 20 at a predetermined position along the ride path 16. For example, the sanitization component 22 may be configured to be activated at a specific location where guests of the amusement park ride are no longer positioned in the ride vehicle 12 (e.g., between an unloading region of the ride path 16 and a loading region of the ride path 16). Accordingly, guests of the amusement park ride do not block or cover any of the surfaces of the ride vehicle 12 to be cleaned by the sanitization component 22. In other embodiments, the sanitization component 22 may be activated along a portion of the ride path 16 where guests are situated in the ride vehicle 12 (e.g., between the loading region and the unloading region with respect to a direction of travel of the ride vehicle 12). As discussed in detail herein with reference to FIG. 6, the sanitization component 22 may include a movable member that expands from and retracts into a compartment of the ride vehicle 12 to position the ultraviolet light source 18 proximate to the surfaces for cleaning. The movable member may be configured to rotate and/or otherwise adjust a position of the ultraviolet light source 18 to expose all surfaces of the ride vehicle 12 commonly contacted by guests to the ultraviolet light 20. In other embodiments, the sanitization component 22 may include the ultraviolet light source 18 that is fixedly mounted to the ride vehicle 12, such that the ultraviolet light source 18 does not move with respect to the ride vehicle 12. The ultraviolet light source 18 may be positioned in the ride vehicle 12 to direct ultraviolet light toward surfaces of the ride vehicle 12 frequently contacted by guests.

Further, the sanitization station 14 may include a dryer or heater 24 that may be utilized to remove liquid droplets from the surfaces of the ride vehicle 12 that accumulate cleaning solution 26 dispensed from the nozzle 21. In certain embodiments, the sanitization station 14 may include a plurality of the nozzles 21, where each of the nozzles 21 is configured to direct the cleaning solution 26 toward the surfaces of the ride vehicle 12. For instance, a first nozzle 21 may direct a mixture of soap and water toward the ride vehicle 12. Additionally, a second nozzle 21, positioned past the first nozzle 21 with respect to a direction of travel of the ride vehicle 12 along the ride path 16, may direct water toward the ride vehicle 12 to remove the mixture of soap and water that accumulates on the ride vehicle 12. In some embodiments, a rate at which the cleaning solution 26 is directed toward the ride vehicle 12 from the nozzles 21 may differ as the ride vehicle 12 travels through the sanitization station 14. For example, the first nozzle 21 may direct the cleaning solution 26 toward the ride vehicle 12 at a higher flow rate than the second nozzle 21, the first nozzle 21 may direct the cleaning solution 26 toward the ride vehicle at a lower flow rate than the second nozzle 21, or the flow rate of the cleaning solution 26 may be substantially the same from the first nozzle 21 and the second nozzle 21.

In any case, the dryer or heater 24 may be utilized to direct air, or warm air, toward the ride vehicle 12 to remove any remaining liquid particles from the soap and water mixture and/or the water, such that the ride vehicle 12 exits the sanitization station 14 substantially dry. The cleaning solution 26 directed from one or more of the nozzles 21 may be utilized in addition to, or in lieu of, the ultraviolet light 20. In some embodiments, the ultraviolet light source 18 is activated to emit the ultraviolet light 20 toward the ride vehicle 12, while the cleaning solution 26 is not directed toward the ride vehicle 12. In other embodiments, the cleaning solution 26 is sprayed or otherwise released from the nozzle 21, while the ultraviolet light source 18 is deactivated. In still further embodiments, both the ultraviolet light 20 and the cleaning solution 26 are directed toward the surfaces of the ride vehicle 12.

Figure 2:
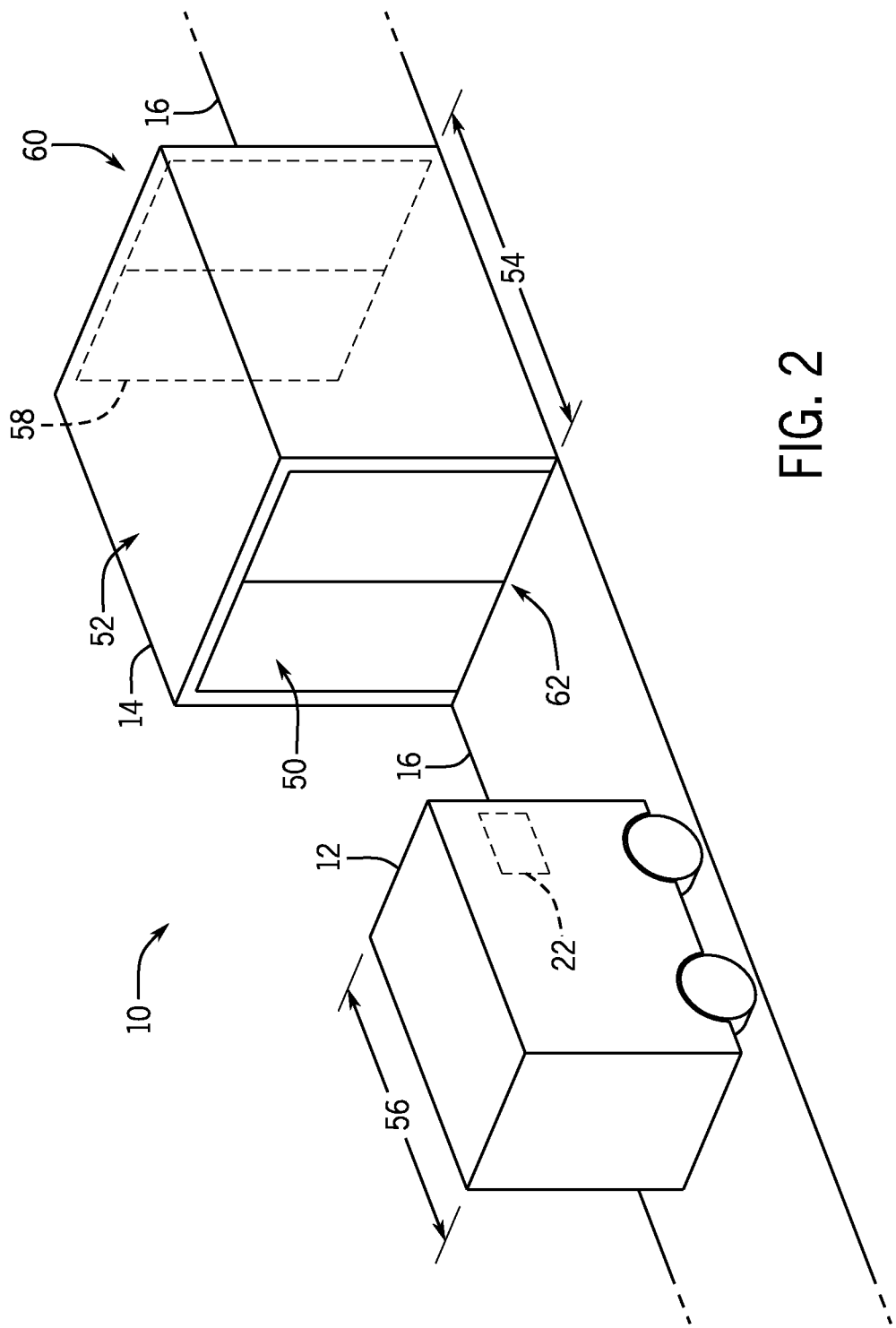
FIG. 2 illustrates a perspective view of an embodiment of a sanitization station of the sanitization system of FIG. 1, in accordance with an aspect of the present disclosure.

As discussed above, the sanitization system 10 is disposed along a portion of the ride path 16 where guests are no longer positioned within the ride vehicle 12. In some cases, the sanitization system 10 is positioned within a viewpoint of the guests (e.g., guests waiting to experience the amusement park ride at the loading region) but the actual sanitization process may be at least substantially blocked from viewing by the guests, which may eliminate incongruity with a theme of the related ride. For example, FIG. 2 illustrates an embodiment of the sanitization system 10 having an access door 50 for blocking the ultraviolet light 20 from the guests. The access door 50 is configured to open (e.g., via an actuator) to enable the ride vehicle 12 to move within a housing 52 of the sanitization system 10. Upon entry into the housing 52, the access door 50 is closed (e.g., via the actuator) and the ride vehicle 12 is covered by (e.g., enclosed within) the housing 52. As such, transmissions of the ultraviolet light 20 are substantially blocked from exiting the housing 52. This may facilitate direction of the ultraviolet light 20 to more areas of the ride vehicle 12. For example, the interior of the access door 50 may be mirrored (along with other aspects of the interior of the housing 52) to redirect the ultraviolet light 20 toward the ride vehicle 12.

In some embodiments, a speed of movement of the ride vehicle 12 is reduced and/or stopped to provide the ride vehicle 12 with sufficient exposure to the ultraviolet light 20. Additionally or alternatively, the speed of movement of the ride vehicle 12 is based on a length 54 of the housing 52. For example, the speed of movement of the ride vehicle 12 is reduced when the length 54 of the housing 52 is relatively short. In some embodiments, the speed of movement of the ride vehicle 12 is completely stopped for a period of time in order for the surfaces of the ride vehicle 12 to obtain sufficient exposure to the ultraviolet light 20. In such embodiments, the length 54 of the housing 52 may be substantially similar to a length 56 of the ride vehicle 12 (e.g., the housing 52 may be sized to accommodate a single ride vehicle 12). In other embodiments, the speed of movement of the ride vehicle 12 is maintained or increased when the length 54 of the housing 52 is relatively long. Additionally or alternatively, the housing 52 may be sized to receive multiple ride vehicles 12. Further, in some embodiments, the ultraviolet light source 18 may move along with the ride vehicle 12 within the housing 52 or otherwise along the ride path 16.

In any case, a second access door 58 is disposed on an end 60 of the housing 52 opposite an end 62 having the access door 50. As such, the second access door 58 is opened to enable the ride vehicle 12 to exit the housing 52 after exposure to the ultraviolet light 20 and continue along the ride path 16 (e.g., toward the loading region). The ride vehicle 12 is thus able to simultaneously and/or periodically travel along the ride path 16 and to receive cleaning as the amusement park ride continuously operates. In some embodiments, the access door 50 and the second access door 58 open and close at substantially the same time based on instructions from a controller. In other embodiments, opening and closing the access door 50 and the second access door 58 may be offset (e.g., the access door 50 is opened and closed to receive the ride vehicle 12, the second access door 58 is subsequently opened and closed to enable the ride vehicle 12 to exit, and so forth), as instructed by a controller. In any case, the timing of the actuation of the access doors 50 and 58 may be dependent on a predetermined exposure time for the ride vehicle 12 or a predetermined length of travel for the ride vehicle 12. In some embodiments, both doors 50 and 58 are kept closed by a controller while a sanitization process is active and then opened by the controller when the sanitization process is complete. As with the first access door 50, the second access door 58 may have a reflecting interior to facilitate redirection of the ultraviolet light 20 back toward the ride vehicle 12.

Figure 3:
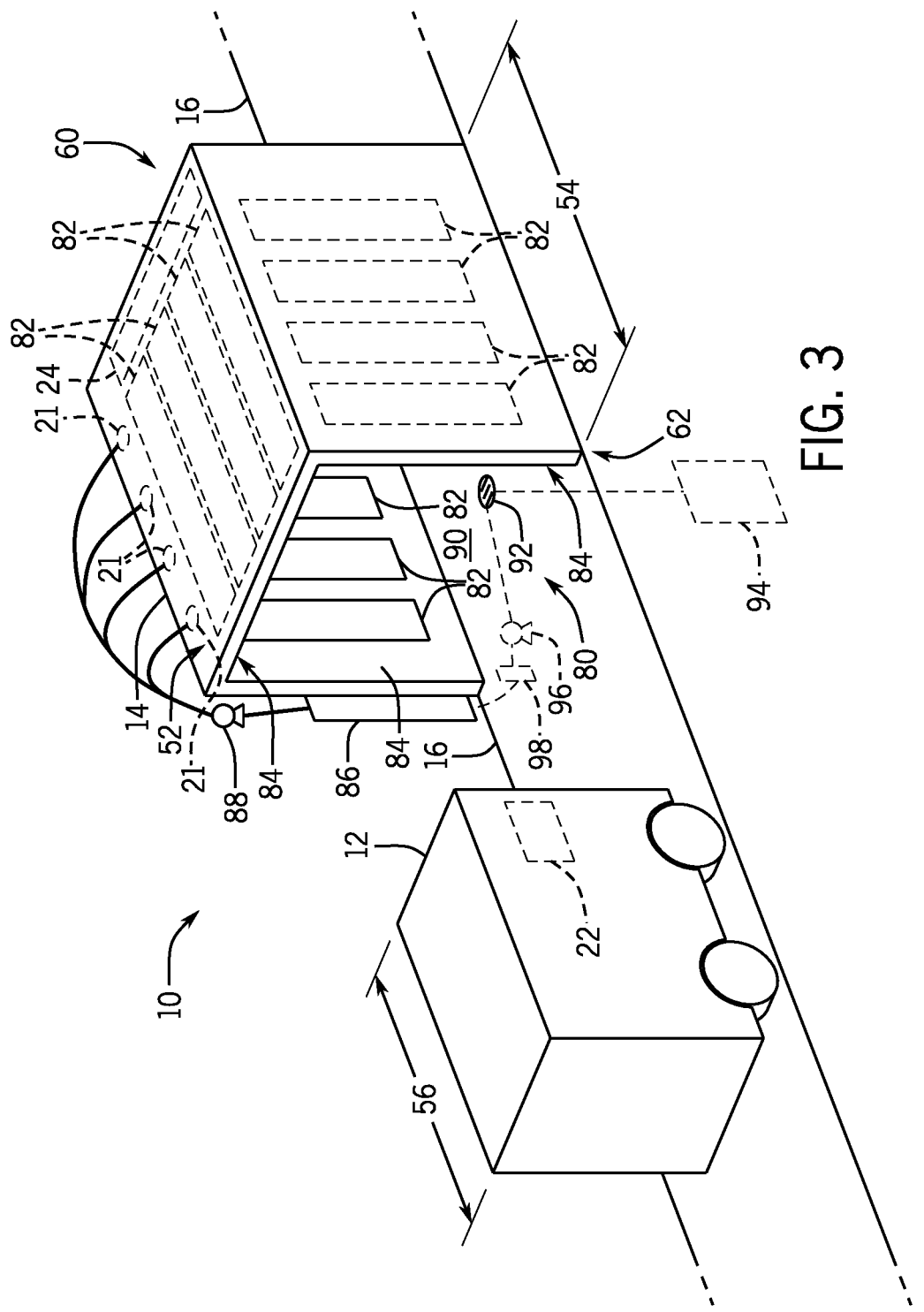
FIG. 3 illustrates a perspective view of an embodiment of the sanitization station of FIG. 2 with an access door in an open position, in accordance with an aspect of the present disclosure.

FIG. 3 illustrates an embodiment of the sanitization system 10 where the access door 50 is in an open position 80. As shown in the illustrated embodiment of FIG. 3, the housing 52 includes one or more ultraviolet light sources 82 disposed on interior walls 84 of the housing 52. Accordingly, the ultraviolet light sources 82 transmit the ultraviolet light 20 toward the ride vehicle 12 when the ride vehicle is disposed in the housing 52. In some embodiments, the ultraviolet light sources 82 are positioned within the housing 52 at varying angles, distances, and locations with respect to the interior walls 84 of the housing 52. Further, the positions of the ultraviolet light sources 82 may be dependent on a configuration (e.g., size, shape, components) of the ride vehicle 12. That is, positioning of the ultraviolet light sources 82 correlate or correspond to the shape of the ride vehicle 12 in certain embodiments. For example, the positions of the ultraviolet light sources 82 may be different for a ride vehicle in the shape of a cart as compared to a ride vehicle shaped as a car. In any case, the ultraviolet light 20 is configured to reach surfaces of the ride vehicle 12 that guests frequently contact (e.g., seats, handles, knobs, buttons) to remove and/or kill bacteria and other undesirable substances from the surfaces.

As discussed above, the sanitization station 14 may include one or more of the nozzles 21 that direct cleaning solution, such as a mixture of soap and water or water, toward surfaces of the ride vehicle 12. Additionally, the sanitization station 14 may include the dryer or heater 24 that is configured to remove residual cleaning solution from the surfaces of the ride vehicle 12 before, or as, the ride vehicle 12 exits the sanitization station 14. As shown in the illustrated embodiment of FIG. 3, the nozzles 21 may receive cleaning solution from a storage tank 86. The cleaning solution 26 may be directed from the storage tank 86 to the nozzles 21 via a pump 88. In some embodiments, each of the nozzles 21 receives the cleaning solution 26 from the storage tank 86 via the pump 88. In other embodiments, each nozzle 21 may include a corresponding storage tank and pump.

Further, the cleaning solution 26 may also collect on a surface 90 of the sanitization station 14. Accordingly, the surface 90 of the sanitization station 14 may include a drain 92 that receives any of the cleaning solution 26 accumulated on the surface 90 and directs the cleaning solution 26 away from the sanitization station. In some embodiments, the drain 92 may direct the cleaning solution 26 to a waste tank 94. The waste tank 94 may be positioned with respect to the drain 92, such that the cleaning solution 26 flows from the drain 92 to the waste tank 94 via gravity. In other embodiments, the drain 92 directs the cleaning solution 26 back toward the storage tank 86, such that the cleaning solution 26 may be recycled and utilized multiple times within the sanitization station 14. A pump 96 may direct the cleaning solution 26 from the drain 92 back to the storage tank 86. Further, a filter 98 may be disposed between the drain 92 and the storage tank 86 to remove particles and/or undesired substances from the cleaning solution 26 before reaching the storage tank 86.

Figure 4:
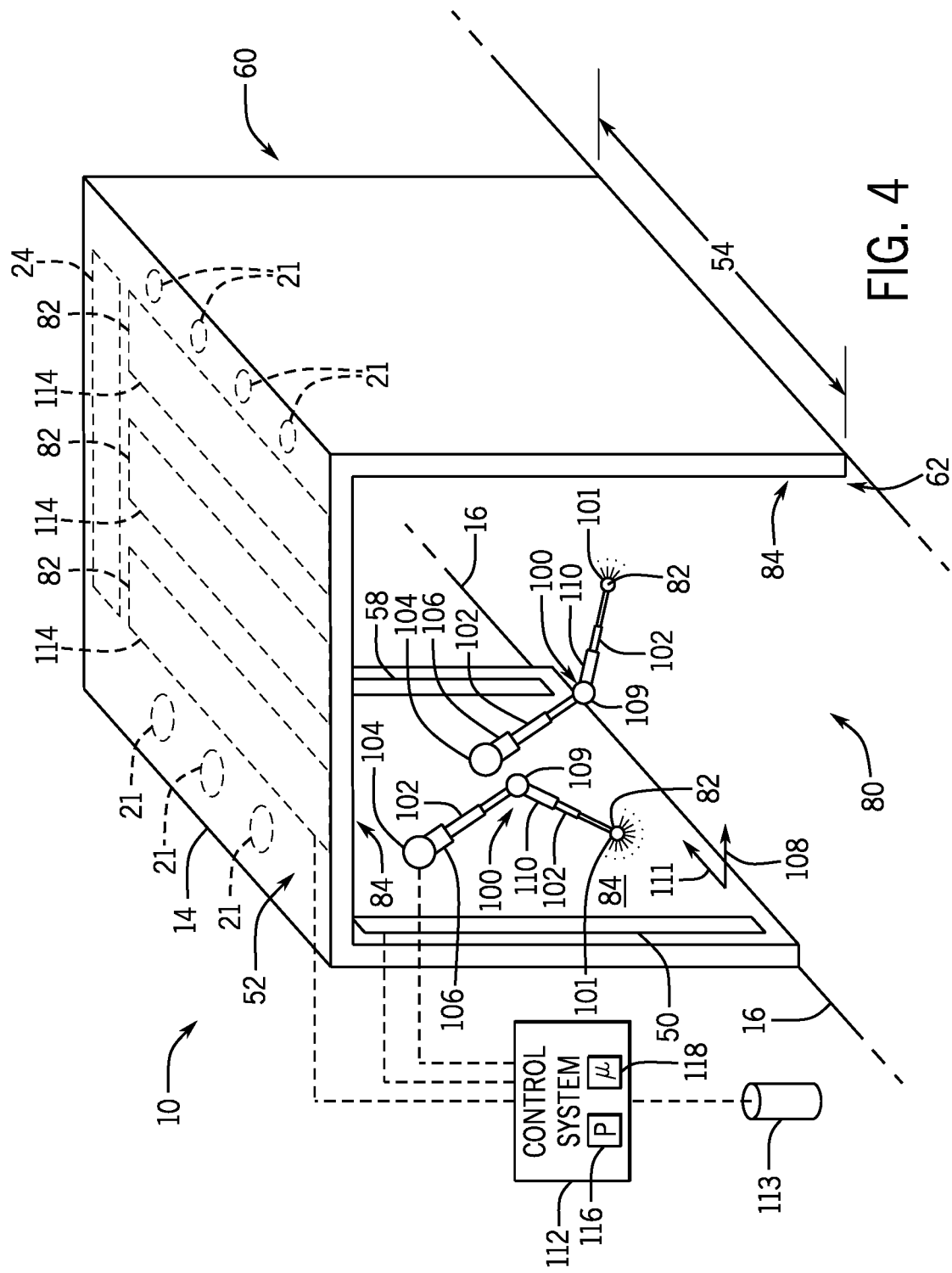
FIG. 4 illustrates a perspective view of an embodiment of the sanitization station of FIGS. 2 and 3 having ultraviolet light sources coupled to one or more movable members, in accordance with an aspect of the present disclosure.

As shown in the illustrated embodiment of FIG. 4, the housing 52 may include one or more movable members 100 that are configured to adjust a position of the ultraviolet light sources 82 with respect to the interior walls 84 of the housing 52. For example, as shown in FIG. 4, the housing 52 may have two movable members 100. Each movable member 100 includes a corresponding ultraviolet light source 101 (e.g., adjustable ultraviolet light sources). Additionally or alternatively, the movable members 100 may include one of the nozzles 21 to direct the cleaning solution 26 toward the ride vehicle 12. In some embodiments, the movable members 100 include telescopic arms 102 configured to expand and retract, toward and away from, the ride vehicle 12. Similarly, the movable members 100 may include a first joint 104 that enables a first telescopic arm 106 to rotate about a first axis 108 with respect to the interior walls 84 of the housing. Additionally or alternatively, the movable members 100 may include a second joint 109 coupling the first telescopic arm 106 to a second telescopic arm 110, thereby enabling rotation of the second telescopic arm 109 to rotate about a second axis 111 with respect to the first telescopic arm 106 and/or the interior walls 84. The movable members 100 may articulate, rotate, expand, contract, ratchet, flex, spin, or perform other movements in accordance with present embodiments to facilitate emission of the ultraviolet light 20 on the surfaces of the ride vehicle 12.

As shown in the illustrated embodiment of FIG. 4, the sanitization system 10 includes a control system 112 coupled to a sensor 113. Additionally, the control system 112 is coupled to the one or more movable members 100 having corresponding ultraviolet light sources 101 and one or more fixed ultraviolet light sources 114. Further, in some embodiments, the control system 112 is coupled to the access door 50 and/or the second access door 58. As such, the control system 112 receives feedback from the sensor 113 indicative of a position of the ride vehicle 12. When the ride vehicle 12 is positioned a predetermined distance from the sanitization station 14 (e.g., the housing 52), the control system 112 opens the access door 50 and/or activates the ultraviolet light sources 101 and/or the one or more fixed ultraviolet light sources 114. The control system 112 may be configured to actuate the access door 50 to the open position 80 when the ride vehicle 12 is proximate to the housing 52 (e.g., within 2 yards, within 5 yards, within 10 yards of the end 62 of the housing 52).

In some embodiments, the sensor 113 may provide feedback to the control system 112 indicative of the ride vehicle 12 being fully positioned within the housing 52. The control system 112 may then actuate the access door 50 to close the access door 50 before activating the ultraviolet light sources 101 and/or the fixed ultraviolet light sources 114. As such, the ride vehicle 12 is enclosed within the housing 52 (e.g., the access doors 50 and 58 are each closed) before ultraviolet light 20 is emitted from the ultraviolet light sources 101 and/or the fixed ultraviolet light sources 114. As such, guests that are close to the ride path 16 are blocked from observing the ultraviolet light 20 because the ultraviolet light 20 is blocked from exiting the housing 52 (e.g., via the access doors 50 and 58). When the control system 112 determines that the ride vehicle is enclosed in the housing 52, the control system 112 may then activate the ultraviolet light sources 101 and/or the one or more fixed ultraviolet light sources 114 when the access door 50 reaches the closed position. The control system 112 may further open the second access door 58 after the ultraviolet light sources 101 and/or the one or more fixed ultraviolet light sources 114 are deactivated after a predetermined amount of time (e.g., a predetermined exposure time). Further still, the control system 112 may actuate the second access door 58 to a closed position upon detecting that the ride vehicle 12 is completely outside of the housing 52 (e.g., a predetermined distance from the end 60 of the housing 52).

In some cases, the movable members 100 are adjusted to expose multiple surfaces of the ride vehicle 12 that are frequently contacted by guests to the ultraviolet light 20. For example, the control system 112 may include a processor 116 that executes instructions (a preprogrammed routine) stored in memory 118. In some embodiments, the memory 118 includes instructions for a predetermined sequence of movements for the movable members 100, where the sequence is based on a configuration (e.g., size, shape) of the ride vehicle 12 and positions of the surfaces of the ride vehicle 12 most frequently contacted by the guests (e.g., handles, hand rails, knobs, buttons, seats). In one embodiment, a geometry of the ride vehicle 12 may be mapped (e.g., via a camera) and used to guide the movable members 100. This may occur as a part of the sanitization process and may accommodate vehicles of different shapes. However, mapping may occur a single time for a set of similarly shaped ride vehicles 12. In other embodiments, the sequence is configured to adjust the position of the movable members 100 to expose substantially all surfaces of the ride vehicle 12 that guests may contact. In any case, the ultraviolet light 20 is transmitted toward the ride vehicle 12 to remove bacteria and other undesirable substances from the surfaces of the ride vehicle 12 in between a loading region of the ride path 16 and an unloading region of the ride path 16.

Figure 5:
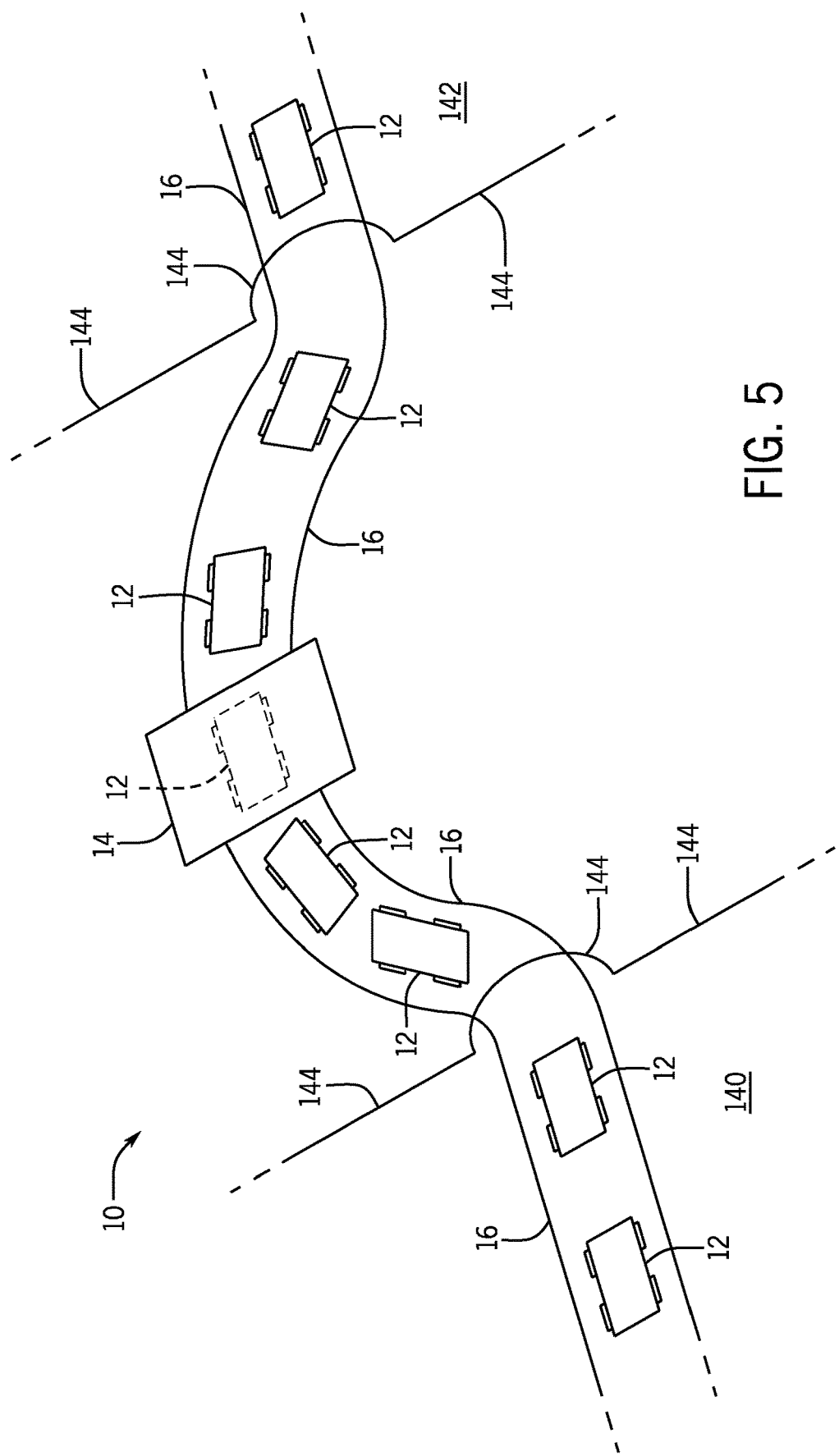
FIG. 5 illustrates a schematic of the sanitization station disposed behind a barrier along a ride path of the amusement park ride, in accordance with an aspect of the present disclosure.

While the embodiments of the sanitization system 10 discussed with respect to FIGS. 2-4 include the access doors 50 and 58 to enclose the housing 52 of the sanitization station 14, other embodiments may not include the access doors 58. For example, FIG. 5 illustrates a schematic of an embodiment of the sanitization station 14 positioned in a portion of the ride path 16 that is blocked from a viewpoint of guests. For example, the ride path 16 includes an unloading region 140 for guests to exit the ride vehicle 12 and experience other attractions at the amusement park. Additionally, the ride path 16 includes a loading region 142 for guests to enter the ride vehicle 12 and experience the amusement park ride associated with the ride vehicle 12. As shown in the illustrated embodiment of FIG. 5, a barrier 144 (e.g., a wall, a tunnel, a room, a compartment) is disposed between the unloading region 140 and the loading region 142 of the ride path 16. The barrier 144 is configured to enable the guests to experience the amusement park ride without viewing the sanitization station 14, which may break the continuity of a themed experience.

In some embodiments, the sanitization station 14 of FIG. 5 does not include the access doors 50 and 58 because the barrier 144 blocks the ultraviolet light 20 from reaching the guests. The ultraviolet light sources 101 and/or the fixed ultraviolet light sources 114 may be continuously running, thereby increasing exposure of the ride vehicle 12 to the ultraviolet light 20 as the ride vehicle 12 moves along the ride path 16. In other words, the ride vehicle 12 may be exposed to the ultraviolet light 20 immediately upon entering the housing 52 without waiting for the ultraviolet light sources 101 and/or the fixed ultraviolet light sources 114 to be activated upon closure of the access doors 50 and/or 58.

Further, the housing 52 of the sanitization station 14 of FIG. 5 may not completely enclose the ride vehicle 12. For instance, the housing 52 may include a plurality of beams and/or other structural support members that are spaced apart from one another, such that the ride vehicle 12 is not completely enclosed or surrounded by walls. However, the ultraviolet light sources 101 and/or the fixed ultraviolet light sources 114 may be mounted to the beams and/or other structural support members of the housing 52 in a similar manner to the interior walls 84 (e.g., FIG. 4).

Figure 6:
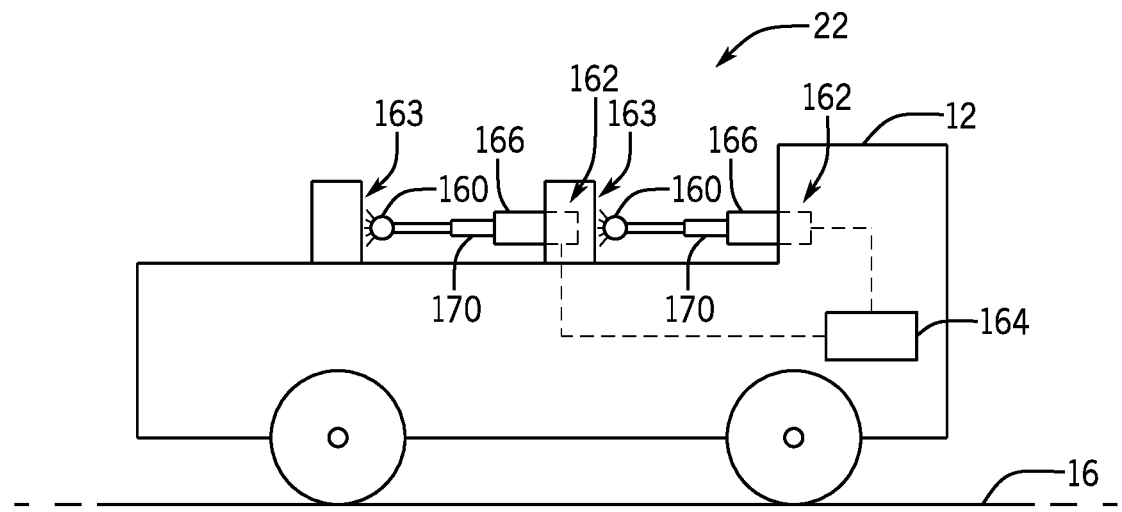
FIG. 6 illustrates an embodiment of a ride vehicle having ultraviolet light sources disposed within compartments of the ride vehicle, in accordance with an aspect of the present disclosure.

FIG. 6 illustrates an embodiment of the ride vehicle 12 that includes ultraviolet light sources 160 that may be disposed in compartments 162 of the ride vehicle 12 during a duration of the ride and actuated toward one or more surfaces 163 of the ride vehicle 12 between the unloading region 140 and the loading region 142 of the ride path 16. For instance, a control system 164 positioned on the ride vehicle 12 (and/or the control system 112 via wireless communication) may actuate movable members 166 that may be disposed in the compartments 162 and configured to direct the ultraviolet light sources 160 toward the one or more surfaces 163 of the ride vehicle, including areas otherwise difficult to access with light (e.g., areas surrounding a floorboard of the ride vehicle 12). The movable members 166 may be actuated once a position of the ride vehicle 12 is detected between the unloading region 140 and the loading region 142 via the sensor 113, for example.

As shown in the illustrated embodiment of FIG. 6, the movable members 166 include telescopic rods 170 that are configured to extend outwardly from the compartments 162 and retract inward toward the compartments 162. In other embodiments, the movable members 166 may include other suitable collapsible, rotating, extendable, flexible, articulating, ratcheting, or otherwise moving arms or members that are configured to direct the ultraviolet light sources 160 toward the surfaces 163 when the ride vehicle 12 is positioned between the unloading region 140 and the loading region 142 and to return the ultraviolet light sources 160 into the compartments 162 when the ride vehicle 12 reaches the loading region 142 (e.g., and when the ride vehicle 12 is between the loading region 142 and the unloading region 140).

In other embodiments, the ultraviolet light sources 160 may not be disposed in the compartments 162. As such, guests may view the ultraviolet light sources 160 during the duration of the ride. In some embodiments, the ultraviolet light sources 160 may be disguised as features on the ride vehicle 12 that are related to a particular theme of the ride. As a non-limiting example, the ultraviolet light sources 160 may be disguised as buttons or mirrors positioned in the ride vehicle 12. In such embodiments, the ultraviolet light sources 160 remain inactive until a position of the ride vehicle 12 is determined to be between the unloading region 140 and the loading region 142 of the ride path 16. As such, the guests do not block the surfaces 163 of the ride vehicle 12 from exposure to the ultraviolet light 20.

Figure 7:
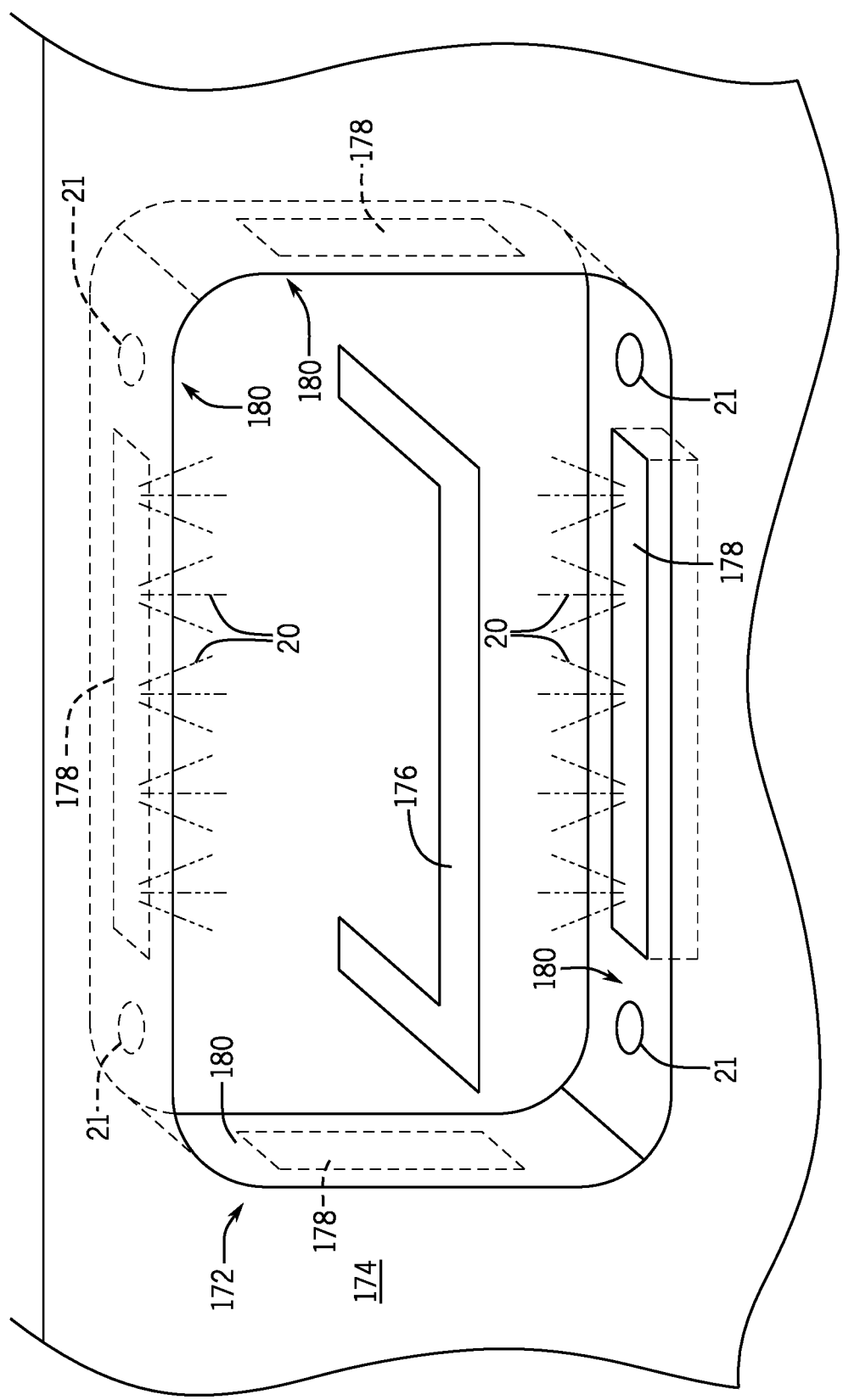
FIG. 7 illustrates a perspective view of an ultraviolet light source disposed in a compartment of a the ride vehicle, in accordance with an aspect of the present disclosure.

FIG. 7 illustrates a perspective view of an embodiment of a compartment 172 that may be disposed in the ride vehicle 12. As used herein, the compartment 172 may include a cutout within a wall 174 of the ride vehicle 12 that includes a handle 176. The handle 176 may be utilized by the guest to open a door of the ride vehicle 12 and/or as a support feature for guests to clasp as the ride vehicle 12 moves along the ride path 16. As shown in the illustrated embodiment of FIG. 7, the compartment 172 may include an ultraviolet light source 178 on one or more surfaces 180. Additionally or alternatively, the surfaces 180 may include one or more of the nozzles 21 configured to direct the cleaning solution 26 toward the handle 176.

The ultraviolet light 20 emitted from the ultraviolet light source 178 and/or the cleaning solution 26 (e.g., water, soap, a mixture of water and soap, a foam, or another suitable cleaning substance) from the nozzles 21 may be utilized to sanitize the handle 176 and/or the one or more surfaces 180 of the compartment 172. The handle 176 and/or the one or more surfaces 180 of the compartment 172 may be frequently contacted by guests of the amusement park ride, which may lead to a transfer of germs, bacteria or undesirable substances that may be removed by the ultraviolet light 20 and/or the cleaning solution 26.

In some embodiments, the ultraviolet light source 178 and/or the nozzles 21 may be substantially flush with the surfaces 180 of the compartment 172, such that the ultraviolet light source 178 and/or the nozzles 21 are at least partially blocked from a viewpoint of the guests. In other embodiments, the ultraviolet light source 178 and/or the nozzles 21 are recessed with respect to the surfaces 180. In any case, the ultraviolet light source 178 and/or the nozzles 21 may be substantially fixed with respect to the compartment 172 and configured to direct the ultraviolet light 20 and/or the cleaning solution 26 toward the handle 176 and/or the surfaces 180 of the compartment 172. The ultraviolet light 20 and/or the cleaning solution 26 may be directed toward the handle 176 and/or the surfaces 180 when the ride vehicle 12 travels along the ride path 16 from the unloading region to the loading region (e.g., with respect to a direction of travel of the ride vehicle 12). In other embodiments, the ultraviolet light 20 and/or the cleaning solution 26 are directed toward the handle 176 and/or the surfaces 180 when guests are positioned within the ride vehicle 12 (e.g., between the loading region and the unloading region with respect to a direction of travel of the ride vehicle 12 along the ride path 16). Accordingly, the ultraviolet light 20 and/or the cleaning solution 26 may be associated with a theme of the amusement park ride, such that guests within the ride vehicle 12 may observe or otherwise experience the ultraviolet light 20 and/or the cleaning solution 26 and associate the ultraviolet light 26 and/or the cleaning solution 26 with an experience of the amusement park ride.

Figure 8:
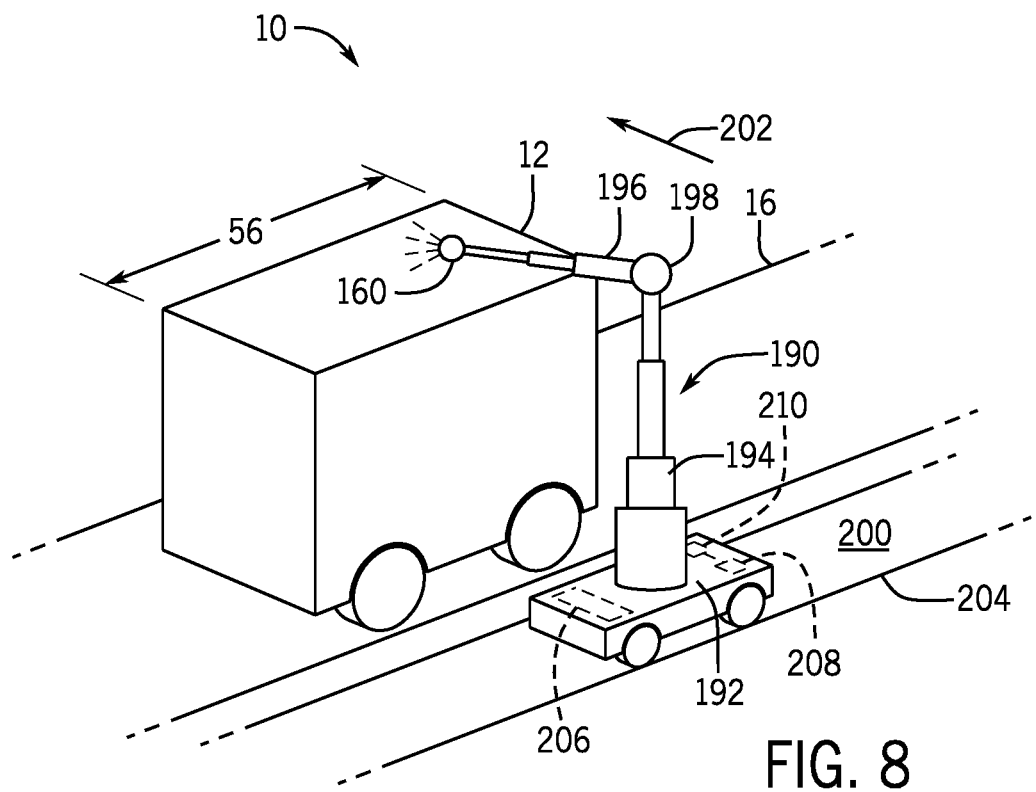
FIG. 8 illustrates a perspective view of an embodiment of an ultraviolet light source coupled to a movable member that is secured to a transportable base, in accordance with an aspect of the present disclosure.

In still further embodiments, the ultraviolet light source 160 may be positioned on a movable member 190 secured to a transportable base 192 that is configured to move along the ride path 16 and alongside the ride vehicle 12. For example, FIG. 8 illustrates a perspective view of an embodiment of the movable member 190 secured to the transportable base 192. As shown in the illustrated embodiment of FIG. 8, the movable member 190 includes a first telescoping arm 194 coupled to a second telescoping arm 196 via a joint 198. The first telescoping arm 194 is configured to adjust a height of the ultraviolet light source 160 with respect to a surface 200 of the ride path 16. Further, the second telescoping arm 196 is configured to adjust a position of the ultraviolet light source 160 with respect to surfaces of the ride vehicle 12. In some embodiments, the joint 198 enables rotation of the second telescoping arm 196 about an axis 202 with respect to the first telescoping arm 194, such that the second telescoping arm 196 may further adjust the position of the ultraviolet light source 160 with respect to surfaces of the ride vehicle 12.

In some embodiments, the transportable base 192 is configured to move along a track 204 positioned adjacent to the ride path 16 of the ride vehicle 12. Accordingly, the transportable base 192 enables the movable member 190, and thus, the ultraviolet light source 160 to move alongside the ride vehicle 12. The track 204 may include various components that drive movement of the transportable base 192, such as belts, magnets, rollers, or other suitable components. In other embodiments, the transportable base 192 includes a motor 206 that drives movement of the transportable base 192 along the track 204.

The transportable base 192 may be configured to move along the track 204 with the ride vehicle 12. In some embodiments, a sensor 208 (e.g., a proximity sensor or other suitable position sensor) is utilized to detect a position of the ride vehicle 12 along the ride path 16. As shown in the illustrated embodiment, the sensor 208 is included on the transportable base 192. In other embodiments, the sensor 208 is positioned adjacent to the ride path 16 and/or in another suitable position to detect the ride vehicle 12. In any case, movement of the transportable base 192 along the track 204 may be initiated or otherwise adjusted based on the feedback from the sensor 208 indicative of the position of the ride vehicle 12 along the ride path 12. For instance, in some embodiments, the transportable base 192 is substantially stationary until the sensor 208 detects that the ride vehicle 12 has reached a predetermined position along the ride path 16. The sensor 208 may be communicatively coupled to a control system 210 of the movable member 190 and/or the motor 206. As such, feedback from the sensor 208 is utilized to direct movement of the transportable base 192 along the track 204. Further still, the sensor 208 may continuously monitor the position of the ride vehicle 12 as the transportable base 192 moves along the track 204. Accordingly, the control system 210 may be configured to substantially match a speed of the transportable base 192 with a speed of the ride vehicle 12 (e.g., within 10% of, within 5% of, or within 1% of the speed of the ride vehicle 12).

Additionally or alternatively, the control system 210 may be configured to adjust a speed of the transportable base 192 and/or a distance that the transportable base 192 travels along the ride path 16 (e.g., via the track 204) based on a desired amount of cleaning for a given ride vehicle 12. For example, in some embodiments, the ride vehicle 12 may include relatively large amounts of undesirable substances (e.g., detected by a camera, a sensor, or an operator) to be removed by the ultraviolet light source 160 (or the cleaning solution 26). The speed and/or travel distance of the transportable base 192 may then be adjusted (e.g., via the control system 210 and/or an operator), such that the ride vehicle 12 is exposed to the ultraviolet light 20 and/or the cleaning solution 26 for a suitable amount of time to remove the undesirable substances. The adjustment may be automatic (e.g., preprogrammed), or may be operator controlled.

In some embodiments, the track 204 may be positioned between the unloading region 140 and the loading region 142 with respect to a direction of movement of the ride vehicle 12 along the ride path 16. As such, guests are not positioned in the ride vehicle 12 and do not block ultraviolet light from reaching surfaces of the ride vehicle 12 when the ultraviolet light source 160 is activated to direct ultraviolet light toward surfaces of the ride vehicle 12. Further, the track 204 may be substantially circular, such that the transportable base 192 moves back toward the unloading region 140 upon reaching the loading region 142 of the ride path 16. Therefore, the track 204 forms a circuit that enables the transportable base 192 to expose surfaces of subsequent ride vehicles 12 that reach the unloading region 140 of the ride path 16.

FIG. 9 illustrates a perspective view of an embodiment of the sanitization station 14 that may include a movable structure 210 that is configured to move with the ride vehicle 12 along at least a portion of the ride path 16. As shown in the illustrated embodiment of FIG. 9, the movable structure 210 includes a first post 212, a second post 214, and a cross post 216, where the cross post 216 couples the first post 212 to the second post 214. Each of the first post 212, the second post 214, and the cross post 216 may include a plurality of ultraviolet light sources 218 configured to transmit the ultraviolet light 20 toward the ride vehicle 12. Additionally or alternatively, the first post 212, the second post 214, and/or the cross post 216 may include one or more of the nozzles 21 configured to direct the cleaning solution 26 (e.g., water, a mixture of soap and water, a cleansing foam, wax, or another suitable substance) toward the ride vehicle 12.

In any case, the movable structure 210 may be configured to move along a pair of tracks 220, where a first track 222 of the pair of tracks 220 is disposed on a first side 224 of the ride path 16 and a second track 226 of the pair of tracks 220 is disposed on a second side 228 of the ride path 16. As such, the first post 212 and the second post 214 may include various components that drive movement of the first post 212 and the second post 214 along the pair of tracks 220, such as belts, magnets, rollers, wheels, or other suitable components.

In certain embodiments, the first post 212 and/or the second post 214 may be configured to rotate about a first axis 230 and a second axis 232, respectively. As such, the movable structure 210 may increase an amount of surfaces of the ride vehicle 12 that receive exposure to the ultraviolet light 20. In other words, as the first post 212 and/or the second post 214 rotate about the first axis 230 and/or the second axis 232, respectively, an angle at which the ultraviolet light 20 is directed toward the ride vehicle 12 is adjusted, thereby exposing additional surfaces of the ride vehicle 12 to the ultraviolet light 12. Additionally or alternatively, the first post 212, the second post 214, and/or the cross post 216 may include bars 234 that are configured to move away from the first post 212 and the second post 214 toward the ride vehicle 12. Accordingly, a position of the plurality of ultraviolet light sources 218 may be adjusted, such that the plurality of ultraviolet light sources 218 is positioned closer to the surfaces of the ride vehicle 12. Further still, the bars 234 may also be configured to rotate about the first axis 230 and/or the second axis 232 to adjust an angle at which the ultraviolet light 20 is directed toward the ride vehicle 12, thereby increasing an amount of surfaces of the ride vehicle 12 exposed to the ultraviolet light 20.

Additionally, the movable structure 210 may be configured to move along the pair of tracks 220 with the ride vehicle 12. In some embodiments, a sensor 236 (e.g., a proximity sensor or other suitable position sensor) is utilized to detect a position of the ride vehicle 12 along the ride path 16. As shown in the illustrated embodiment, the sensor 236 is included on movable structure 210. In other embodiments, the sensor 236 is positioned adjacent to the ride path 16 and/or in another suitable position to detect the ride vehicle 12. In any case, movement of the movable structure 210 along the pair of tracks 220 may be initiated or otherwise adjusted based on the feedback from the sensor 236 indicative of the position of the ride vehicle 12 along the ride path 12. For instance, in some embodiments, the movable structure 210 is substantially stationary until the sensor 236 detects that the ride vehicle 12 has reached a predetermined position along the ride path 16. The sensor 236 may be communicatively coupled to a control system 238 of the movable structure 210. As such, feedback from the sensor 236 is utilized to direct movement of the movable structure 210 along the pair of tracks 220. Further still, the sensor 236 may continuously monitor the position of the ride vehicle 12 as the movable structure 210 moves along the pair of tracks 220. Accordingly, the control system 238 may be configured to substantially match a speed of the movable structure 210 with a speed of the ride vehicle 12 (e.g., within 10% of, within 5% of, or within 1% of the speed of the ride vehicle 12).

Additionally or alternatively, the control system 238 may be configured to adjust a speed of the movable structure 210 and/or a distance that the movable structure 210 travels along the ride path 16 (e.g., via the pair of tracks 220) based on a desired amount of cleaning for a given ride vehicle 12. For example, in some embodiments, the ride vehicle 12 may include relatively large amounts of undesirable substances (e.g., detected by a camera, a sensor, or an operator) to be removed by the plurality of ultraviolet light sources 218 (or the nozzles 21). The speed and/or travel distance of the movable structure 210 may then be adjusted (e.g., via the control system 238 and/or an operator), such that the ride vehicle 12 is exposed to the ultraviolet light 20 and/or the cleaning solution 26 for a suitable amount of time to remove the undesirable substances. The adjustment may be automatic (e.g., preprogrammed), or may be operator controlled.

Figure 10:
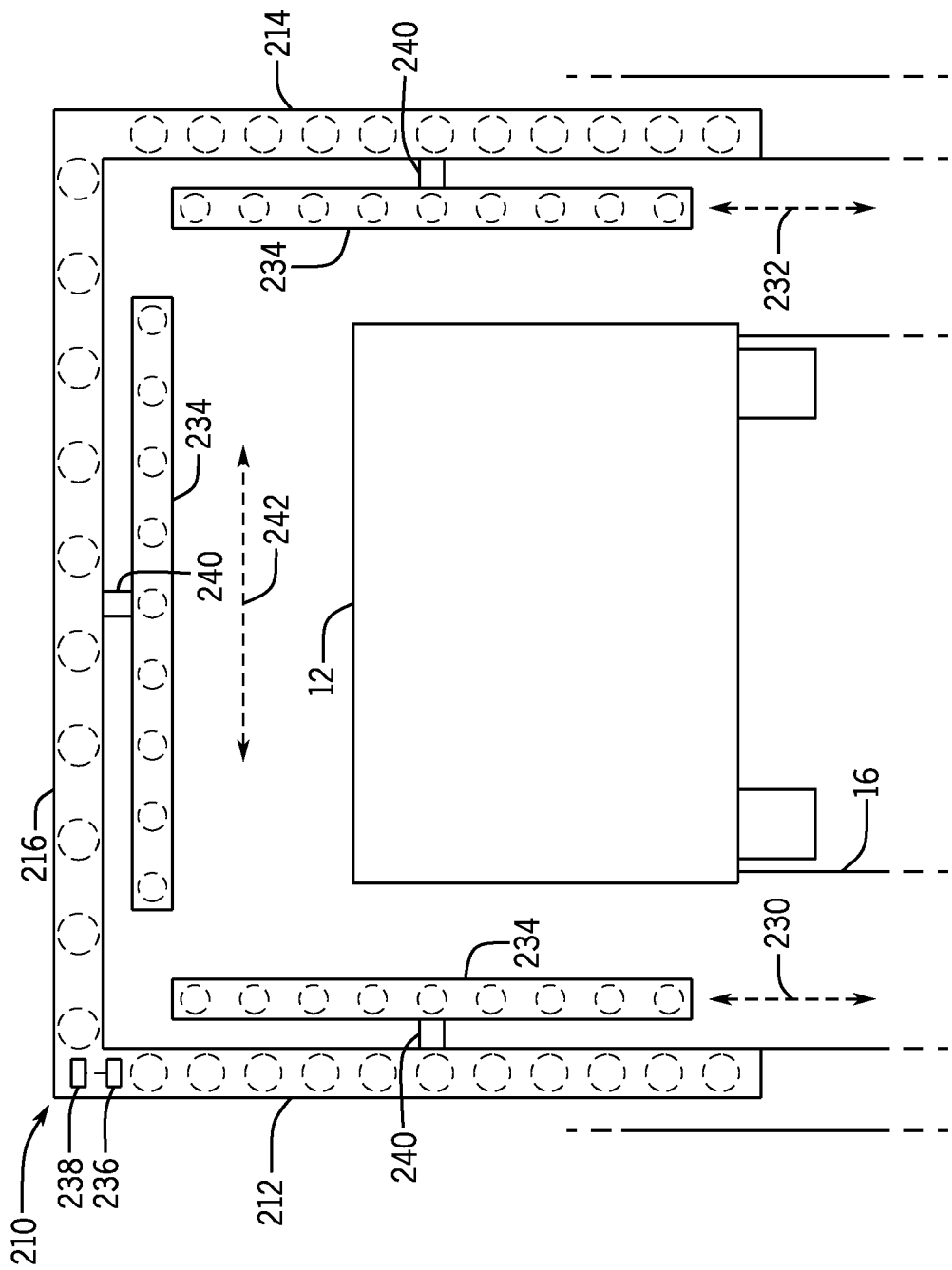
FIG. 10 illustrates an elevation view of an embodiment of the movable ultraviolet light source assembly of FIG. 9, in accordance with an aspect of the present disclosure.

FIG. 10 is an elevation view of the ride vehicle 12 and the movable structure 210. As shown in the illustrated embodiment of FIG. 10, each of the first post 212, the second post 214, and the cross post 216 include a corresponding bar 234. The bars 234 may be coupled to the first post 212, the second post 214, and/or the cross post 216 via a telescoping mount 240. The telescoping mount 240 may enable movement of the bars 234 toward and away from the first post 212, the second post 214, and the cross post 216. Additionally or alternatively, the telescoping mounts 240 may enable rotation of the bars 234 about the first axis 230, the second axis 232, and/or a third axis 242. As such, the movable structure 210 enables the ultraviolet light 20 and/or the cleaning solution 26 to be directed toward surfaces of the ride vehicle 12 at multiple angles and/or multiple distances from the surfaces of the ride vehicle 12.

In some embodiments, the movable structure 210 is configured to move along the ride path 16 with the ride vehicle 12 between the unloading region 140 and the loading region 142 with respect to a direction of travel of the ride vehicle 12 along the ride path 16. In other embodiments, the movable structure 210 may move along the ride path 16 at another suitable location. The sanitization station 14 may include multiple movable structures 210 disposed along the ride path 16 that enable cleaning of multiple ride vehicles 12 simultaneously. Further, each of the multiple movable structures 210 may be configured to travel along a predetermined portion of the ride path 16 and direct ultraviolet light 20 and/or cleaning solution 26 toward the ride vehicle 12 currently within the predetermined portion. In other embodiments, each of the multiple movable structures 210 may be configured to move along a circular circuit similar to the track 204 discussed above with respect to FIG. 8.

Figure 11:
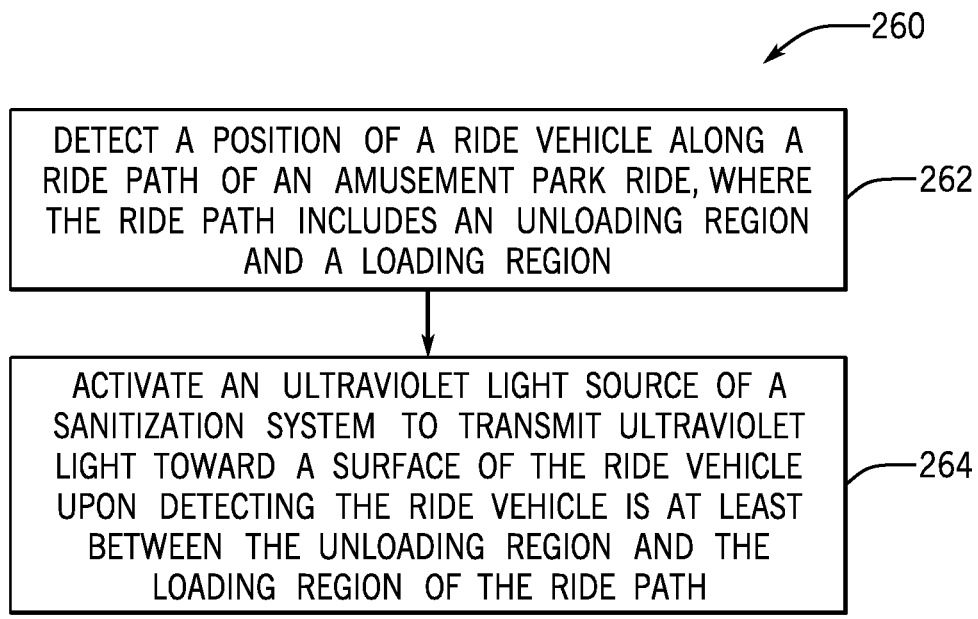
FIG. 11 is a flow chart of an embodiment of a process for operating the sanitization system of FIGS. 1-7, in accordance with an aspect of the present disclosure.

FIG. 11 is a block diagram of a process 260 for operating the sanitization system 10. For example, at block 262, the control system 112 may receive feedback from the sensor 113 (or another suitable sensor) indicative of a position of the ride vehicle 12 along the ride path 16 and/or a sensor (e.g., camera) providing information related to whether something within the vehicles is blocking exposure (e.g., an article left in a ride vehicle). In some embodiments, the control system 112 may be configured to receive feedback from a plurality of sensors that are disposed at various locations along the ride path 16, such that the control system 112 detects the position of the ride vehicle 12 as the ride vehicle moves along the entire ride path 16. In other embodiments, the control system 112 may detect the position of the ride vehicle 12 when the ride vehicle 12 is within a predetermined distance from the sanitization station 14, when the ride vehicle 12 is between the unloading region 140 and the loading region 142, or both. In some embodiments, a sensor may also detect whether something in the ride vehicle 12 would block the ultraviolet light 20 from reaching certain surfaces (e.g., trash left in the vehicle) and this may be utilized by the control system 112 to control the sanitation system 10.

Further, at block 264, the control system 112 is configured to activate the ultraviolet light sources 101, the fixed ultraviolet light sources 114, the ultraviolet light sources 160, and/or the plurality of ultraviolet light sources 218 to transmit the ultraviolet light 20 toward surfaces of the ride vehicle 12 when the control system 112 detects that the ride vehicle 12 is at least between the unloading region 140 and the loading region 142. Further, the control system 112 may delay activation of the ultraviolet light sources 101, the fixed ultraviolet light sources 114, the ultraviolet light sources 160, and/or the plurality of ultraviolet light sources 218 until the control system 112 receives feedback indicative of the ride vehicle 12 being positioned within the predetermined distance from the sanitization station 14, other location information, and/or whether something has been identified within the ride vehicle 12.

Additionally, in some embodiments, the control system 112 may be configured to actuate the access door 50 of the housing 52 of the sanitization station 14 upon detecting that the ride vehicle 12 is within a predetermined distance from the housing 52. For example, the predetermined distance for actuating the access door 50 may be greater than the predetermined distance for actuating the ultraviolet light sources 101 and/or the fixed ultraviolet light sources 114. The control system 112 may also be configured to adjust a position of the ultraviolet light sources 101 and/or the plurality of ultraviolet light sources 218 with respect to the surface of the ride vehicle 12 using the movable members 100 mounted within the housing 52 of the sanitization station 14 and/or the bars 234 mounted to the movable structure 210 of the sanitization station 14. For example, the movable members 100 may be mounted to the interior walls 84 of the housing 52, such that the movable members 100 adjust the position of the ultraviolet light sources 101 with respect to the interior walls 84. As such, the ultraviolet light sources 101 may transmit the ultraviolet light 20 toward one or more surfaces of the ride vehicle 12.

Additionally or alternatively, the control system 112 may be configured to activate the ultraviolet light sources 160 and/or 178 positioned on board the ride vehicle 12. As discussed above, the ultraviolet light sources 160 may be disposed within compartments 162 and/or 172 of the ride vehicle 12 when the ride vehicle 12 is positioned between the loading region 142 and the unloading region 140. Once the control system 112 determines that the ride vehicle 12 is between the unloading region 140 and the loading region 142 (e.g., a portion of the ride path 16 where guests are not present on the ride vehicle 12), the control system 112 actuates the movable members 166 to eject the ultraviolet light sources 160 from the compartments 162, such that the ultraviolet light sources 160 may transmit the ultraviolet light 20 toward the surfaces of the ride vehicle.

While only certain features of the disclosure have been illustrated and described herein, many modifications and changes will occur to those skilled in the art. It is, therefore, to be understood that the appended claims are intended to cover all such modifications and changes as fall within the true spirit of the present disclosure. The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

The invention claimed is:

1. An amusement park ride sanitization system, comprising:
a ride path of an amusement park ride;
an amusement ride vehicle configured to travel along the ride path; and
a sanitization station disposed along the ride path, wherein the sanitization station comprises:
an ultraviolet light source configured to transmit ultraviolet light toward a surface of the amusement ride vehicle; and
a control system configured to detect a position of the amusement ride vehicle along the ride path and to activate the ultraviolet light source when the control system determines that the amusement ride vehicle is positioned at a particular position along the ride path.

2. The amusement park ride sanitization system of claim 1, wherein the ride path comprises an unloading region for a guest to exit the amusement ride vehicle and a loading region for the guest to enter the amusement ride vehicle.

3. The amusement park ride sanitization system of claim 1, comprising an additional ultraviolet light source configured to transition into and out of a compartment of the amusement ride vehicle.

4. The amusement park ride sanitization system of claim 3, wherein the control system is configured to adjust a position of the additional ultraviolet light source toward the surface of the amusement ride vehicle when the control system determines that the amusement ride vehicle is transferring from past the unloading region to the loading region of the ride path.

5. The amusement park ride sanitization system of claim 1, wherein the ride path comprises a barrier configured to block a view of an interior of a housing of the sanitization station from a loading region and an unloading region along the ride path.

6. The amusement park ride sanitization system of claim 1, comprising a disinfectant sprayer or mister.

7. The amusement park ride sanitization system of claim 1, comprising a first telescoping arm configured to adjust a height of the ultraviolet light source with respect to a surface of the ride path.

8. The amusement park ride sanitization system of claim 7, comprising a second telescoping arm coupled to the first telescoping arm via a joint, wherein the second telescoping arm is configured to adjust a position of the ultraviolet light source with respect to the first telescoping arm.

9. The amusement park ride sanitization system of claim 8, wherein the joint enables rotation of the second telescoping arm about an axis with respect to the first telescoping arm.

10. A system, comprising:
an amusement park ride, comprising a ride path and a ride vehicle, wherein the ride vehicle is configured to transport a guest along the ride path in a ride direction of the amusement park ride, and wherein the ride path comprises an unloading region for the guest to exit the ride vehicle and a loading region for the guest to enter the ride vehicle; and a sanitization station disposed along the ride path such that the sanitization station is past the unloading region and before the loading region of the ride path along the ride direction of the amusement park ride, wherein the sanitization station comprises:

a housing configured to receive the ride vehicle as the ride vehicle travels along the ride path;

an ultraviolet light source configured to transmit ultraviolet light toward a surface of the ride vehicle; and a control system configured to detect a position of the ride vehicle along the ride path and to activate the ultraviolet light source when the control system determines that the ride vehicle is positioned at a particular position relative to the housing.

11. The system of claim 10, wherein the ultraviolet light source is disposed on a movable member configured to adjust a position of the ultraviolet light source with respect to the surface of the ride vehicle.

12. The system of claim 11, wherein the control system comprises a memory configured to store a predetermined sequence of positions to adjust the position of the ultraviolet light source with respect to the surface of the ride vehicle.

13. The system of claim 11, wherein the movable member is mounted to an interior wall of the housing, wherein the movable member comprises a first telescopic arm configured to extend and retract the ultraviolet light source with respect to the interior wall.

14. The system of claim 13, wherein the movable member comprises a second telescopic arm coupled to the first telescopic arm via a joint that enables movement between the first telescopic arm and the second telescopic arm.

15. The system of claim 11, wherein the movable member is disposed on a transportable base configured to travel along the ride path, and wherein the movable member comprises a telescopic arm configured to extend toward and retract from the ride vehicle.

16. The system of claim 10, wherein the housing comprises an access door configured to enclose the ride vehicle within the housing, and wherein the control system is configured to actuate the access door when the ride vehicle is positioned at a second particular position along the ride path.

17. A method, comprising:

detecting a position of a ride vehicle as the ride vehicle travels along a ride path of an amusement park ride using a sensor coupled to a control system, wherein the ride path comprises an unloading region for a guest to exit the ride vehicle and a loading region for the guest to enter the ride vehicle; and activating, using the control system, an ultraviolet light source of a sanitization system to transmit ultraviolet light toward a surface of the ride vehicle upon detecting that the ride vehicle is traveling from the unloading region to the loading region of the ride path.

18. The method of claim 17, comprising actuating, using the control system, an access door of a housing of the sanitization system upon detecting that the ride vehicle is within a distance from the housing.

19. The method of claim 17, comprising actuating, using the control system, a position of the ultraviolet light source with respect to the surface of the ride vehicle using a movable member mounted within a housing of the sanitization system.

20. The method of claim 17, comprising actuating, using the control system, the ultraviolet light source from a compartment of the ride vehicle.

* * * * *